United States Patent [19]

Danner

[11] 4,311,346
[45] Jan. 19, 1982

[54] TRACK ASSEMBLY HINGE JOINT

[75] Inventor: Bill A. Danner, Rochester, Ill.

[73] Assignee: Fiat-Allis Construction Machinery, Inc., Deerfield, Ill.

[21] Appl. No.: 53,362

[22] Filed: Jun. 29, 1979

[51] Int. Cl.³ .................... F16J 15/32; B62D 55/20
[52] U.S. Cl. ................................ 305/11; 305/14; 305/58 R; 277/58; 277/39; 277/152
[58] Field of Search .................... 305/11, 14, 58 R; 277/35, 25, 37, 38, 39, 40, 91, 92, 58, 63, 82, 181–185, 94, 188 A, 152; 308/168, 239, 175

[56] References Cited

U.S. PATENT DOCUMENTS

| 2,750,214 | 6/1956 | Bermingham | 277/25 |
| 3,409,336 | 11/1968 | Dadds | 305/11 |
| 4,062,550 | 12/1977 | Satsumabayashi et al. | 277/92 |
| 4,094,516 | 6/1978 | Morley et al. | 305/11 X |
| 4,179,130 | 12/1979 | Fass et al. | 277/92 X |
| 4,185,838 | 1/1980 | Danner | 305/11 X |
| 4,199,199 | 4/1980 | Granda | 305/58 R |

FOREIGN PATENT DOCUMENTS 732091  4/1966  Canada ................................ 305/11

OTHER PUBLICATIONS

Sargent; "Kahr Special Bearings", Kahr Bearing Division, Catalog 77; 1977, pp. 4-A2 & 4-A4 & 6-1.

Primary Examiner—David A. Scherbel
Attorney, Agent, or Firm—August E. Roehrig, Jr.; John A. Doninger

[57] ABSTRACT

A track assembly hinge joint for a track of an endless track vehicle, in which track links are connected by a pin and bushing, is formed by securing the ends of the pin in bores in the ends of a pair of spaced link members and securing the bushing in the inner portions of bushing and pin accommodating bores in the ends of the adjoining pair of link members, with a self-lubricating bearing sleeve disposed between the bushing and the pin and with a self-lubricating washer disposed between each end of the bushing and a side thrust control ring on which a radially inner element of a two-element lip type seal is mounted for cooperation with an outer seal element which is seated in the outer end portion of the bore in the associated link member adjacent the end of the bushing.

4 Claims, 2 Drawing Figures

TRACK ASSEMBLY HINGE JOINT

BACKGROUND OF THE INVENTION

This invention relates to hinge joints and is more particularly concerned with improvements in hinge joints which are particularly adapted for connecting link elements of a track for an endless track vehicle.

Hinge joint arrangements for connecting track links have heretofore been employed which have included various type seals and in which a track link counterbore has served as a seal cavity. In such arrangements, all mating parts must be held to very close tolerances which gives rise to increased costs in manufacturing and to assembly problems when the tolerance requirements are not met. This type of hinged joint when pressed together to form a track rail assembly becomes a blind assembly which is controlled by location of the holes in the track link for mounting the track shoes. In most cases, due to the number of mating parts, and the relationship to each other, the sealing of such joints is very difficult.

In the commonly used track assembly hinge joint there is a radial space between the track bushing and track pin which allows for uneven loading between the pin and bushing and results in a much greater wear rate than normal. Also, this radial spacing between the track bushing and the track pin permits a considerable amount of abrasive contaminants to enter when the seal fails and produces rapid deterioration of the hinged joints so that frequent repair or replacement of the deteriorated elements of the track mechanism is required. Other difficulties arising from the loose fit between the bushing include track stretching, which is referred to as pitch elongation. When the track stretches and the distance from one bushing to the next increases, the track pitch no longer matches sprocket pitch and the bushing starts to ride up in the tooth resulting in wear on the tooth and on the outside of the bushing, with the track becoming snaky and the sprocket teeth gouging into the links. Loose snaky track caused by bushing and pin wear speeds up wear of the roller flanges and link rails due to the slamming action of the links against such members.

It is a general object of the present invention to provide an improved joint arrangement of this type which reduces wear, which minimizes damage when there is any seal failure, and which can be manufactured and assembled with greater economy than the joint arrangements of similar character heretofore employed.

It is a more specific object of the present invention to provide a new and improved hinge joint arrangement which is particularly adapted for connecting track links of endless track vehicles.

It is a further object of the invention to provide a track link hinge joint connection which is more wear resistant than the joints presently employed and which minimizes track stretching so as to avoid development of a snaky track condition and the difficulties resulting from such a track condition.

Another object of the invention is to provide a track hinge joint structure in which the washer used for thrust control is allowed to float between the pin and the seal with the washer held in contact with the end face of the bushing and thereby eliminating the risk of developing metal fragments which otherwise frequently result from contact between the bushing and the metal spacer and which may migrate into the bushing especially when the track is working on a side slope.

Still another object of the invention is to provide a hinge joint of the type described in which self-lubricating bearing elements are employed between the bushing and the pin and also between the end of the bushing and the thrust control ring so that the bushing fits on the pin with a minimum degree of looseness thereby reducing wear and track stretching and in which an efficient sealing arrangement is employed for preventing entry of contaminants and absorbing end thrust with the seal adapted to be installed in pre-assembled relation in the bushing end of the link and eliminating any need for a counterbore and the close tolerances heretofore required in this type installation.

The invention which is claimed herein comprises a hinge joint construction of the type in which one hinge element in the form of a bushing is mounted on a hinge pin which comprises the cooperating hinge element, with provision for some degree of axial movement of the bushing on the pin, together with bearing and sealing elements which comprise a self-lubricating bearing sleeve disposed between the pin and the bushing and a self-lubricating bearing washer between the end face of the bushing and an end thrust control ring on the pin on which an element of an end seal assembly is carried with a cooperating seal element seated in a bore in which the end of the bushing is mounted.

The foregoing objects and other objects and advantages of the invention will become more apparent when reference is made to the accompanying detailed description of the preferred embodiment of the invention which is set forth therein and shown in the accompanying drawings wherein like reference numerals indicate corresponding parts throughout.

DESCRIPTION OF THE PREFERRED EMBODIMENT

Figure 1:
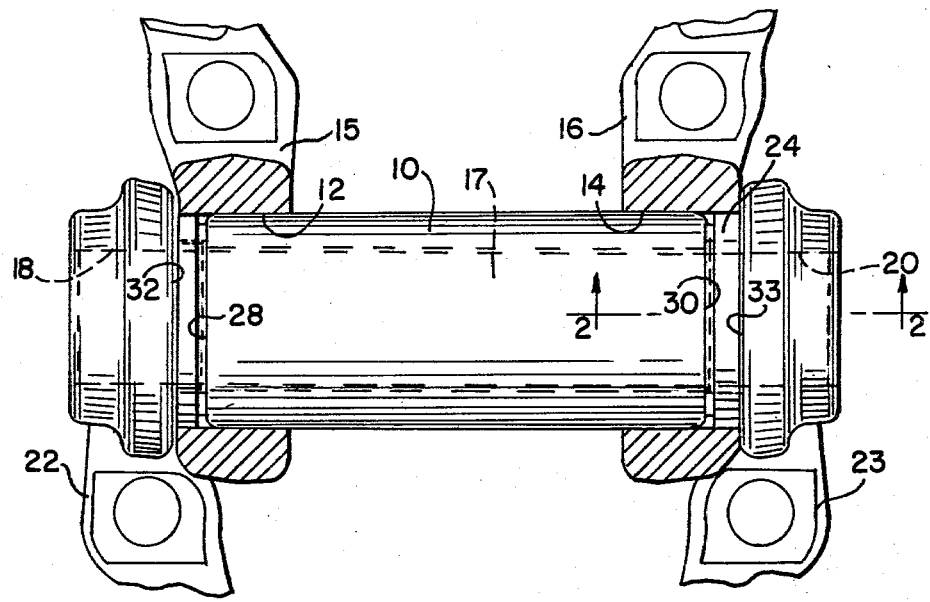
FIG. 1 is a plan view, with a portion in section, of a track link hinge joint which incorporates the principal features of the invention.

The hinge joint of the present invention is particularly adaptable for hingedly connecting track links, as illustrated, but may be employed in different installations, the track link joint being typical. In the joint shown, a track bushing 10 has opposite ends press fit in the inner portions of bored holes 12, 14 in the inner ends of a pair of spaced link bar members 15 and 16, and is mounted on a pin 17. The pin 17 extends at its ends outboard of the link members 15 and 16 and is secured in bores 18 and 20 in the ends of a cooperating pair of adjoining link bar members 22 and 23 so as to form a pivot connection between the two pairs of link members 15, 16 and 22, 23. A seal structure 24 is employed at each end of the bushing 10 to prevent the entry of contaminants into the lubrication areas which could damage or cause excessive wear of the contacting surfaces when there is relative movement between the bushing 10 and pin 17. The joint which is illustrated is designed to connect the link elements in a track assembly of the type employed on crawler tractors and similar vehicles, which comprises a plurality of connected link structures mounted for travel on drive sprockets and idler wheels (not shown) and carrying ground-engaging plate-like shoe members (not shown).

Figure 2:
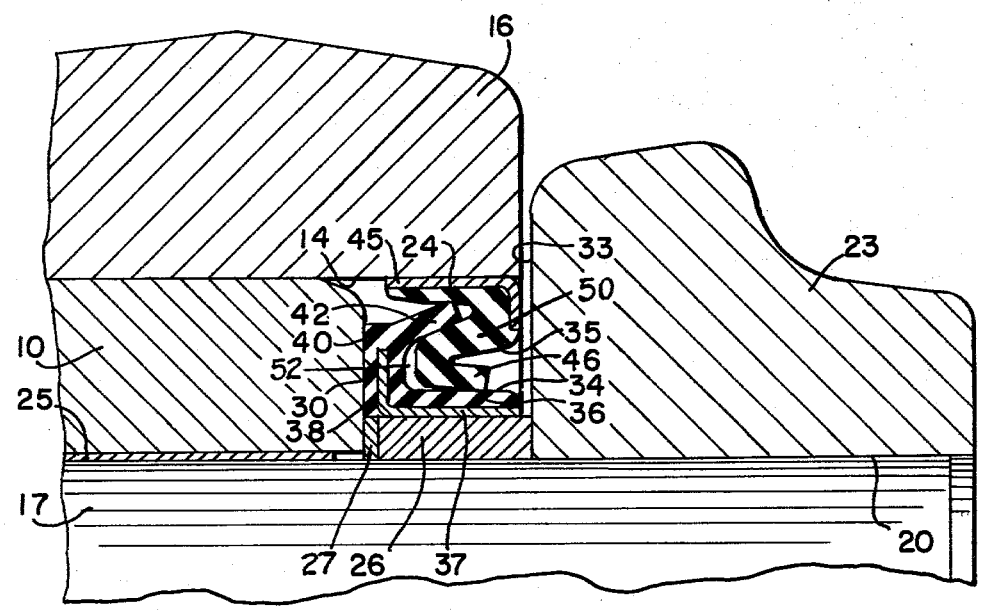
FIG. 2 is a cross sectional view, to an enlarged scale, the view being taken on line 2—2 of FIG. 1.

As shown in FIG. 2, the bushing 10 is assembled on the pin 17 with a liner in the form of a tube 25 of relatively thin wall material of the type employed in self-lubricating bearing installations which will fit tight on the pin 17 and permit rotative movement of the bushing 10 relative to the pin 17. A suitable tube material for the liner 25 is available from Kahr Bearing Division of Sargent Industries at Burbank, Calif., and is marketed under the name Kahr-Lon. It is understood to consist of thermoset plastic resins, Teflon particles and reinforcing synthetic fibers. A metal thrust control spacer ring 26 is press fit on the pin 17 in the space between each end 28 and 30 of the bushing 10 and the confronting inner wall 32, 33 at the ends of the associated link member 22, 23. A thrust bearing washer 27 is interposed between the spacer 26 and each end face or end wall 28, 30 of the bushing 10, which is formed of self-lubricating material of the same character as tube 25.

The seal structure 24 at each end of the bushing 10 comprises two seal elements 34 and 35 which may be pre-assembled and mounted in the space between the end faces 28, 30 of the bushing 10 and the inner faces 32, 33 of the ends of the link bar members 22, 23. The ends of the bushing 10 are secured in the inner end portions of the bores 12 and 14 in the link bar members 15 and 16 which results in a recess being formed in the outer portions of the bores in which the seal assemblies 24 are received.

The annular inner or internal seal element 34 is generally U-shaped and positioned in axially outwardly opening relation with the base portion 36, which is faced by one flange of a metal reinforcing ring 37, seated on the radially outside face of the spacer ring 26. The reinforcing ring 37 has an angular cross section with the adjoining radially directed flange 38 buried in the axially inner portion of the body of the seal element. The U-shaped seal element 34 is of rubber or elastomeric resilient composition. The axially inner face 40 of the element 34 which extends in a radial plane is positioned in abutting relation with the end face 30 of the bushing 10. A sealing lip formation 42 extends in an axially outward direction and is radially spaced from the base portion 36.

The annular outer or external seal element 35 is generally S- or Z-shaped in cross section and has a metal reinforcing ring 45 of angular cross section mounting the assembly in the end of the bore 14 with the annular ring formation press fit in the outboard end of the bore 14 and forming the base for the element 35. The resilient element 35 has a lip formation 46 which extends axially outwardly and, when in assembled relation for operation, resiliently bears against the outboard face of the base portion 36 of the element 34 with portions adjacent to the formation 45 extending into the area between the lip formation 42 on the internal seal element and the base forming ring formation 45 and in sealing contact with the lip formation 42. The lip formation 42, when the elements are in assembled and working relation, engages in the axially inwardly opening recess formed between the base forming ring formation 45 and the body portion 50 of the external seal element 35 so that there is a labyrinth 52 formed between the lip contacting points.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A hinge joint for connecting track elements of an endless track vehicle which comprises a bushing secured at its ends to the spaced ends of a pair of link plates and a pin received in the bushing and secured at its ends to the ends of a pair of adjoining link plates which are disposed outboard of the bushing carrying link plates, an axial movement limiting ring member secured on said pin adjacent each end of the bushing, a sleeve member secured on the pin and disposed between the bushing and the pin which sleeve member is formed of self-lubricating material, a washer formed of self-lubricating material secured on the pin at each end of the bushing which is disposed adjacent the end face of the bushing and the end face of said axial movement limiting ring member and a seal assembly mounted on said ring member at each end of the bushing, said seal assembly comprises an inner seal element which has a face engaging the end face of said bushing, a base portion which is seated on said movement limiting ring member, and an annular sealing lip extending in an outward axial direction and an outer seal element having an annular sealing lip which extends in an axial direction and is in resilient engagement with an outer radial face of said base portion of said inner sealing element, said outer seal element further having an outer base portion, said annular sealing lip of said inner seal element being in resilient engagement with an inner radial face of said outer base portion, and said base portion of said inner seal element is disposed between an outer radial face of said movement limiting ring member and the radially inner most portion of said outer seal element.

2. A hinge joint as set forth in claim 1 wherein said bushing has its ends secured in axially aligned bores in the ends of said bushing carrying link plates and wherein said seal assembly is located at each end of the bushing.

3. A hinge joint as set forth in claim 1 wherein said outer seal element has an annular groove opening in an axial inward direction into which the sealing lip on the inner seal element extends.

4. A hinge joint as set forth in claim 1 wherein said bushing has its ends secured in axially aligned bores in the ends of said bushing-carrying link plates, which bushing ends are disposed in inboard portions of said axially aligned bores in the supporting link plates, and said seal assembly includes axially inner and outer seal elements with the outer seal element seated in outboard portions of the bores in said bushing supporting link plates.

* * * * *